United States Patent
Dong et al.

(10) Patent No.: US 12,247,173 B2
(45) Date of Patent: Mar. 11, 2025

(54) ENERGY-SAVING PROCESS AND DEVICE FOR RECOVERING C2 FROM REFINERY DRY GAS

(71) Applicant: DALIAN UNIVERSITY OF TECHNOLOGY, Dalian (CN)

(72) Inventors: Hongguang Dong, Dalian (CN); Wenchang Chang, Dalian (CN); Haotian Ye, Dalian (CN); Jilong Jia, Dalian (CN); Zhizhong Han, Dalian (CN)

(73) Assignee: DALIAN UNIVERSITY OF TECHNOLOGY, Liaoning (CN)

( * ) Notice: Subject to any disclaimer, the term of this patent is extended or adjusted under 35 U.S.C. 154(b) by 206 days.

(21) Appl. No.: 18/014,442

(22) PCT Filed: Oct. 15, 2020

(86) PCT No.: PCT/CN2020/121060
§ 371 (c)(1),
(2) Date: Jan. 4, 2023

(87) PCT Pub. No.: WO2022/077314
PCT Pub. Date: Apr. 21, 2022

(65) Prior Publication Data
US 2023/0332061 A1 Oct. 19, 2023

(51) Int. Cl.
*C10G 70/04* (2006.01)
(52) U.S. Cl.
CPC ... *C10G 70/046* (2013.01); *C10G 2300/4006* (2013.01); *C10G 2300/4012* (2013.01); *C10G 2300/4081* (2013.01)

(58) Field of Classification Search
CPC .......... C10G 70/046; C10G 2300/4006; C10G 2300/4012; C10G 2300/4081;
(Continued)

(56) References Cited

U.S. PATENT DOCUMENTS

2018/0170839 A1* 6/2018 Kurukchi .................. C07C 7/04
2021/0348071 A1* 11/2021 Luo ........................ C07C 11/04
2022/0389337 A1* 12/2022 Shao .................. B01D 53/1425

FOREIGN PATENT DOCUMENTS

| CN | 104419464 A | 3/2015 |
| CN | 104557386 A | 4/2015 |

(Continued)

*Primary Examiner* — Ali Z Fadhel
(74) *Attorney, Agent, or Firm* — Muncy, Geissler, Olds & Lowe, P.C.

(57) ABSTRACT

The preset invention provides an energy-saving process and device for recovering C2 from refinery dry gas. The process is as follows: dry gas is cooled and then sent to a multi-stage absorption tower for treatment; the gas phase from the multi-stage absorption tower is sent to a fuel gas pipeline network or PSA unit, and the liquid phase is sent to a high-pressure flash zone for treatment; the gas phase from the high-pressure flash zone is returned to a compression section of a dry gas pretreatment system; the gas phase from the low-pressure flash zone is sent to a C2 concentrated gas compressor system; and the gas phase from the desorption tower is mixed with the gas phase obtained from the low-pressure flash zone and sent to an ethylene cracking furnace as a C2 concentrated gas product, most of the liquid phase is returned to the multi-stage absorption tower.

12 Claims, 2 Drawing Sheets

(58) Field of Classification Search
CPC .......... Y02P 20/10; Y02P 20/50; B01D 53/00; B01D 53/02; B01D 53/75; C07C 7/00; C07C 7/11; C07C 9/06; C07C 70/04
See application file for complete search history.

(56) References Cited

FOREIGN PATENT DOCUMENTS

| | | |
|---|---|---|
| CN | 109045929 A | 12/2018 |
| CN | 112410070 A | 2/2021 |
| CN | 112410071 A | 2/2021 |
| WO | WO2011127036 A1 | 10/2011 |

* cited by examiner

ENERGY-SAVING PROCESS AND DEVICE FOR RECOVERING C2 FROM REFINERY DRY GAS

TECHNICAL FIELD

The present invention belongs to the technical field of refinery dry gas recovery, and particularly relates to an energy-saving process and device for recovering C2 from refinery dry gas.

BACKGROUND

Dry gas comes from the refining unit and chemical unit in the refinery. The dry gas of the refining unit mainly comes from primary and secondary processing of crude oil, such as an atmospheric and vacuum distillation unit, a fluid catalytic cracking unit, a deep catalytic cracking unit and a delayed coking unit, and the dry gas of the chemical unit mainly comes from an alkane dehydrogenation unit, a PSA unit, a light hydrocarbon recovery unit, an ethylbenzene-styrene unit, etc. At present, most of the dry gas produced by refineries in China is burned as fuel, and some is even burned in the torch, which results in low value in use as well as serious waste of resources and environmental pollution.

The main components of refinery dry gas are methane, ethane, ethylene, propylene, propane, butane, etc., among which the content of ethane and ethylene is the highest. The recovery of ethane and ethylene from the dry gas will bring huge economic benefits and effectively prevent environmental pollution. After dry gas recovery, ethylene in C2 can be used as the raw material of ethylbenzene, ethylene oxide, etc., and ethane is an ideal cracking raw material. Ethane is recovered from the refinery and sent to an ethylene production unit, which reduces the cost of cracking raw materials and greatly improves the economic benefits.

At present, the main methods for recovering C2 components from refinery dry gas are cryogenic separation, cold oil absorption, pressure swing adsorption (PSA), etc. Each method has advantages and disadvantages. After decades of development and improvement, the cryogenic separation method has mature technology, perfect process and high product purity and recovery rate, and is a common method for purifying and cracking ethylene in the past. However, the method generally requires gas separation at a low temperature of about $-100°$ C., leading to large cooling load and complex refrigerating flow, and also requires pretreatment of raw gas, leading to large investment in the unit. In addition, the cryogenic separation method is usually suitable for regions with concentrated refineries and a large amount of dry gas by-products. In view of the relatively small and dispersed refineries in China, the economical efficiency of this method is poor. The PSA method can realize normal temperature operation with high degree of automation, simple operation, low energy consumption and environmental friendliness. However, this method has huge equipment, complex control system, low purity of ethylene and low recovery rate, and usually requires multi-stage PSA to obtain polymer grade ethylene, which increases floor area and equipment investment.

The cold oil absorption method belongs to physical absorption, and realizes dry gas separation by using the difference in the solubility of each component of the dry gas in the absorbent. The absorbent is generally mixed C4, mixed C5 and liquefied gas. First, non-condensable gas components such as methane and hydrogen are removed by absorption, and then C2 and C3 components are recovered by desorption. The cold oil absorption method includes middle cold oil absorption ($-40°$ C.$\sim-20°$ C.) and shallow cold oil absorption (above $0°$ C.). The current cold oil absorption technology has the problems of large amount of lean solvent circulation, complete thermal desorption and high energy consumption.

Patent CN 109553504 A proposes a method and device for recovering refinery saturated dry gas using a shallow cold oil absorption technology. The process is composed of compression, absorption, desorption, reabsorption and re-desorption. The absorption temperature is $5°$ C.$\sim15°$ C., and the operating conditions are mild. However, due to high absorption temperature, the amount of solvent circulation is large, the energy consumption of the device is high, and the content of C3 and heavy components in the absorbed methane hydrogen is also high, resulting in the need for two absorption-desorption systems and making the flow complex.

Patent CN 104892340 A discloses a three-tower device and method for recovering ethylene and ethane by oil absorption of dry gas. By increasing cooling and flashing in front of the desorption tower and reducing the operating temperature for absorption, the recovery rate of methane is increased and the content of methane in ethylene products is reduced. However, the technical essence of cooling and flashing is equivalent to adding a condenser system at the top of the desorption tower, and the flash tank is equivalent to a gas-liquid buffer tank behind the fractional condenser, which is finally equivalent to secondary separation of methane and ethylene by means of fractional condensation, achieving the goal of improving the recovery rate of methane, but the problem of high energy consumption of the process is not solved.

Patent CN 101063048 A discloses a method for separating refinery dry gas by means of middle cold oil absorption. The process is composed of compression, dry gas pretreatment, absorption, desorption, cold energy recovery and coarse fractionation. The invention uses refinery liquefied gas as absorbent and sets a cold box-expander system to recover lost absorbent and C2, which has the advantages of low cost of absorbent, low loss, high recovery rate of C2 and no need for ethylene refrigeration compressor. However, the absorbent of the process is all the recycled lean solvent from the bottom of the desorption tower, and the recovered C2 is obtained by thermal desorption of the desorption tower, resulting in large amount of lean solvent circulation, large desorption load, high energy consumption of the unit, and large equipment investment.

Patent CN 102382680 A proposes a combined process of a fluid catalytic cracking absorption and stabilization system and C3 middle cold oil absorption. Through the combination between units, the large amount of continuous circulation of C3 and C2 in the desorbed gas between absorption and desorption is avoided. However, the coupling between units increases the complexity of the flow, and does not fundamentally solve the problems of high solvent consumption and high energy consumption of the unit.

Patent CN 101371966 A proposes a new PSA process for recovering ethylene and hydrogen from refinery dry gas. The process is composed of desulfurization, decarburization, drying, PSA recovery of ethylene and PSA purification of hydrogen. The process has the advantages of low energy consumption, simple operation and environmental friendliness. However, the PSA method has the problems of high impurity content in products, inability to completely separate the main components of refinery dry gas, huge investment and large land occupation.

To sum up, the existing process for recovering C2 and C3 from refinery dry gas generally has the problems of large amount of solvent circulation and high energy consumption. Therefore, to solve the above problems, a new energy-saving process for recovering refinery dry gas is developed.

SUMMARY

In order to realize reliable recovery and utilization of refinery dry gas and solve the problems of large amount of solvent circulation and high energy consumption, the present invention provides an energy-saving process and device for recovering C2 from refinery dry gas. The process adopts the middle cold oil absorption technology to recover C2 components from refinery dry gas by means of multi-stage absorption, multi-stage flash in high- and low-pressure zones and desorption, and the obtained C2 concentrated gas can be directly sent to an ethylene cracking furnace, so the process has high recovery rate, low adsorbent consumption and simple flow. Compared with the traditional oil absorption process, the total investment and energy consumption of the device can be reduced by more than 20%, greatly reducing the economic cost of the refinery gas recovery process.

The present invention provides an energy-saving process for recovering C2 from refinery dry gas, comprising the following steps:
(1) Sending refinery dry gas treated through deacidification, drying and compression by a dry gas pretreatment system to a multi-stage absorption tower for treatment after cooling, sending the gas phase at the top of the tower obtained from the multi-stage absorption tower to a fuel gas pipeline network or PSA unit after cold energy recovery, and sending the liquid phase at the bottom of the tower obtained from the multi-stage absorption tower to a high-pressure flash zone for treatment;
(2) Arranging multiple stages of high-pressure zone flash tanks in the high-pressure flash zone, and returning the gas phase obtained by flash to the compression section of the dry gas pretreatment system; and recycling one part of the obtained liquid phase back to the multi-stage absorption tower as a semi-lean solvent, and sending the other part to a low-pressure flash zone for treatment;
(3) Arranging multiple stages of low-pressure zone flash tanks in the low-pressure flash zone, sending the gas phase, C2 concentrated gas, obtained by flash to a C2 concentrated gas compressor system, recycling one part of the obtained liquid phase back to the multi-stage absorption tower as a secondary lean solvent, and sending the other part to a desorption tower for treatment;
(4) Mixing the gas phase obtained from the desorption tower with the gas phase from the low-pressure flash zone and sending to an ethylene cracking furnace as C2 concentrated gas, returning most of the liquid phase obtained from the desorption tower to the multi-stage absorption tower as a lean solvent, sending a small part out of the battery limit as extracted C4, and supplementing fresh C4 adsorbent.

The specific operating principle is as follows:
The incipient flow of the present invention is consistent with that of the cryogenic process and the middle cold oil absorption process, and the dry gas enters a separation unit after pretreatment, drying and pressurization. The process is used to treat refinery dry gas after pretreatment (deacidification, drying and compression) (3~5 MpaG). The dry gas can be by-product dry gas from atmospheric and vacuum distillation, hydrotreating, reforming, coking and other units, and the source of the dry gas is not specifically limited.

In the present invention, mixed C4 is selected as adsorbent, the recycled lean solvent is composed of 80~95 mol % of C4 and the balance of a small amount of C3 and C5, the recycled secondary lean solvent is composed of 50~80 mol % of C4, and the recycled semi-lean solvent is composed of 30~70 mol % of C4.

The adsorbent used in the present invention is not limited to C4 fraction, and can be various absorbents commonly used in the art to meet the above absorption requirements. Specifically, the adsorbent can be C3 fraction, C4 fraction or C5 fraction commonly used in the art, preferably the alkane component in C3, C4 and C5 fractions, and further preferably C4 fraction containing n-butane and isobutane or liquefied gas containing saturated C3 fraction and C4 fraction. The above C3 adsorbent and C4 adsorbent can be refinery liquefied gas or mixed C4 components. The present invention has no special limit on the amount of adsorbent, which can be determined by those skilled in the art according to the actual situation. This is known to those skilled in the art, and will not be repeated here.

In step (1), the compressed dry gas is cooled to $-15°$ C.~$-40°$ C., and propylene refrigeration is used for cooling. In combination with the operating temperature of other equipment in the process, the propylene refrigeration adopts primary to tertiary refrigeration.

In step (1), the number of theoretical plates of the multi-stage absorption tower is preferably 30~60, the operating pressure is 3~5 MpaG, the tower top temperature is preferably $-15°$ C.~$-35°$ C., and the tower bottom temperature is preferably $-10°$ C.~$-30°$ C. The multi-stage absorption tower is not provided with a reboiler and a condenser, and is provided with a plurality of intercoolers in the upper section and the lower section, preferably two intercoolers. The intercooler in the upper section recovers the cold energy of the liquid phase from the low-pressure zone flash tanks to the desorption tower, and the intercooler in the lower section uses $-40°$ C. propylene refrigeration.

This part of the technology should be understood as that: after pre-cooling, the pretreated and pressurized refinery dry gas enters the bottom of the multi-stage absorption tower to be in countercurrent contact with the semi-lean solvent, the secondary lean solvent and the lean solvent in sequence to absorb C2 and heavier components in the material, and unabsorbed hydrogen and methane gas are mainly obtained at the top of the multi-stage absorption tower and then sent to the fuel gas pipeline network or PSA unit for hydrogen recovery after cold energy recovery.

In step (2), at least one flash tank is arranged in the high-pressure zone. When a plurality of flash tanks are arranged, the flash tanks are successively depressurized and connected in series, and the pressure of the last flash tank is 0.1~0.3 MpaG. The gas phase obtained from each flash tank in the high-pressure flash zone is sent to the corresponding compressor stage of the compression section of the dry gas pretreatment system according to the pressure, one part of the obtained liquid phase is recycled back to the multi-stage absorption tower as a semi-lean solvent, and the other part is sent to the low-pressure flash zone. The liquid phase entering the low-pressure flash zone is the liquid phase of the last flash tank, and the semi-lean solvent can be the liquid phase of each flash tank. The semi-lean solvent enters the lower section of the multi-stage absorption tower, the feed plate is preferably 20~45, and the temperature of the semi-lean solvent is −10° C.~−40° C.

This part of the technology should be understood as that: the absorbed light components such as methane and hydrogen are separated by vacuum flashing, sent to a dry gas compression system, mixed with the feed and then returned to the multi-stage absorption tower, which can improve the recovery rate of methane and hydrogen and reduce the content of methane and hydrogen in the final C2 concentrated gas. The recovery rate of methane and hydrogen can be adjusted by flashing pressure so that the content of methane and hydrogen is low and controllable. The C2 concentrated gas can be directly used as the raw material for ethylene cracking. By extracting the semi-lean solvent in the high-pressure flash zone, the amount of the lean solvent can be greatly reduced, the subsequent treatment capacity of the desorption tower can be reduced, and finally the energy consumption can be reduced.

In step (3), at least one flash tank is arranged in the low-pressure zone. When a plurality of flash tanks are arranged, the flash tanks are successively depressurized and connected in series, and the pressure of the last flash tank is 0~0.1 MpaG. The gas phase obtained from the low-pressure flash zone, as a part of the C2 concentrated gas, enters the C2 concentrated gas compressor for pressurization and is sent out of the battery limit. The C2 concentrated gas compression system adopts multi-stage compression. One part of the obtained liquid phase is recycled back to the multi-stage absorption tower as the secondary lean solvent, and the other part is sent to the desorption tower. The liquid phase sent to the desorption tower is the liquid phase of the last flash tank, and the secondary lean solvent can be the liquid phase of each flash tank. The secondary lean solvent enters the middle part of the multi-stage absorption tower, the feed plate is preferably 5~25, and the temperature of the secondary lean solvent is −30° C.~−70° C.

This part of the technology should be understood as that: part of the C2 components is recovered through vacuum flashing instead of thermal desorption, and the content of C4 heavy component in the recovered C2 product gas and C2 flash volume is controlled by adjusting the flashing pressure, so as to reduce the subsequent desorption volume of the C2 desorption tower and reduce energy consumption. By setting the circulation of the secondary lean solvent, the amount of the lean solvent can be further reduced, the subsequent treatment capacity of the C2 desorption tower can be reduced, and the energy consumption can be further reduced.

In step (4), the remaining C2 and C3 components are recovered by means of thermal desorption in the C2 desorption tower. The number of theoretical plates of the C2 desorption tower is 20~60, the operating pressure is 0.5~4 MpaG, the tower top temperature is −35° C.~45° C., and the tower bottom temperature is 60° C.~160° C.

This part of the technology should be understood as that: after a part of the C2 product is recovered by vacuum flashing, the remaining C2 and C3 components are recovered by means of thermal desorption in the desorption tower. The C2 concentrated gas obtained at the top of the tower is mixed with the C2 concentrated gas recovered by vacuum flashing and then sent to the ethylene cracking furnace as the final C2 concentrated gas. Most of the liquid phase obtained from the bottom of the tower is cooled to −15° C.~−40° C. as the lean solvent through heat recovery and then returned to the top of the multi-stage absorption tower, and the remaining small part is sent out of the battery limit. To ensure the flow of the lean solvent in the system, further preferably, fresh C4 adsorbent is supplemented during the cooling process of the lean solvent. The present invention has no special requirements for the temperature of the supplemented fresh C4 adsorbent.

This part of the technology should be understood as that: in the present invention, the purpose of sending the extracted part of the liquid phase from the bottom of the desorption tower out of the battery limit and supplementing fresh C4 absorbent is to prevent the accumulation of heavy components in the solvent, which may cause the bottom temperature of the desorption tower to be too high and affect the absorption effect and the stable operation of the device. According to the different composition of dry gas raw material, the extracted amount from the bottom of the desorption tower and the supplemented amount of the fresh C4 absorbent are also different. If the dry gas raw material contains a large amount of heavy components above C4, the amount to be extracted and supplemented is large. If the dry gas raw material contains a small amount of heavy components, the amount to be extracted is small or only intermittent extraction is required.

In steps (3) and (4), the obtained C2 concentrated gas mainly contains 30~90 mol % of C2, 10~50 mol % of C3 and methane which is less than 5 mol % and controllable, and can be directly used as the raw material for ethylene cracking.

In the present invention, the desorption tower is provided with a reboiler to ensure that the recovery rate and purity of the C2 concentrated product obtained from the top of the tower meet the process requirements, and the heating medium of the reboiler can be low low-pressure steam, or refinery low temperature hot oil or low temperature hot water.

The present invention also provides an energy-saving device for recovering C2 from refinery dry gas:

The device comprises a dry gas pretreatment system, a dry gas precooler, a multi-stage absorption tower, high-pressure zone flash tanks, low-pressure zone flash tanks, a desorption tower, a C2 concentrated gas compressor system and a lean solvent cooling heat exchanger;

The outlet of the dry gas pretreatment system is communicated with the dry gas precooler;

The outlet of the dry gas precooler is communicated with the bottom of the multi-stage absorption tower;

The bottom of the multi-stage absorption tower is communicated with the first-stage high-pressure zone flash tank;

The top of the high-pressure zone flash tank is communicated with the dry gas pretreatment system, and the bottom of each stage of high-pressure zone flash tank is connected with the inlet of the next stage of flash tank, wherein a pipeline at the bottom of one or multiple stages of flash tanks is connected with the lower part of the multi-stage absorption tower, and the bottom of the last stage of flash tank is connected with the inlet of the first-stage low-pressure zone flash tank;

The top of the low-pressure zone flash tank is communicated with the C2 concentrated gas compressor system, and the bottom of each stage of low-pressure zone flash tank is connected with the inlet of the next stage of flash tank, wherein a pipeline at the bottom of one or multiple stages of flash tanks is connected with the middle part of the multi-stage absorption tower, and the bottom of the last stage of flash tank is connected with the inlet of the desorption tower;

The top of the desorption tower is connected with a production pipeline of C2 concentrated gas products, and a pipeline at the bottom of the tower is divided into two branches: one is communicated with the lean solvent cooling heat exchanger, and the other is an extracted C4 pipeline; and a pipeline for supplementing fresh C4 is connected with a lean solvent pipeline;

The outlet of the lean solvent cooling heat exchanger is connected with the top of the multi-stage absorption tower.

In the device of the present invention, the communication and connection modes between devices and between pipelines and devices can be set as required, and the devices are not limited to the connection modes described above.

The present invention has the following beneficial effects:
(1) In the present invention, the methane and hydrogen components in the rich solvent are recovered by means of high-pressure flashing, which improves the recovery rate of methane and hydrogen and reduces the content of methane in the C2 concentrated gas, so that the content of methane in the C2 concentrated gas is low and controllable and the C2 concentrated gas can be directly used as the raw material for ethylene cracking;
(2) In the present invention, low-pressure flashing is used to replace partial thermal desorption, thereby reducing the subsequent recovery from the top of the C2 desorption tower and reducing the load of the C2 desorption tower;
(3) In the present invention, the method of multi-stage absorption is adopted to make full use of the semi-lean solvent, the secondary lean solvent and the lean solvent, which reduces the amount of lean solvent circulation, thereby reducing energy consumption of the device and equipment investment;
(4) In the present invention, the amount of absorbent entrained in the light component gas of methane and hydrogen at the top of the multi-stage absorption tower is small, and it is not necessary to arrange a cold-box and expander system or reabsorption system, which greatly reduces equipment investment;
(5) In the present invention, except for the pipeline for the circulation of the secondary lean solvent, the minimum operating temperature of other systems is not lower than −40° C. Therefore, the devices and pipelines of the systems can be made of ordinary low temperature carbon steel, saving equipment investment.

DESCRIPTION OF DRAWINGS

In the figures: 1 dry gas pretreatment system; 2 dry gas precooler; 3 multi-stage absorption tower; 4 high-pressure zone flash tank; 5 low-pressure zone flash tank; 6 C2 concentrated gas compressor system; 7 desorption tower; 8 lean solvent cooling heat exchanger; A refinery dry gas; B absorbed tail gas; C C2 concentrated gas; D lean solvent; E secondary lean solvent; F semi-lean solvent; G extracted C4; and H fresh C4 adsorbent.

DETAILED DESCRIPTION

The technical solution of the present invention will be clearly and fully described below. Apparently, the described embodiments are merely part of the embodiments of the present invention, not all of the embodiments. Based on the embodiments of the present invention, all other embodiments improved or adjusted by those ordinary skilled in the art will belong to the protection scope of the present invention.

Figure 1:
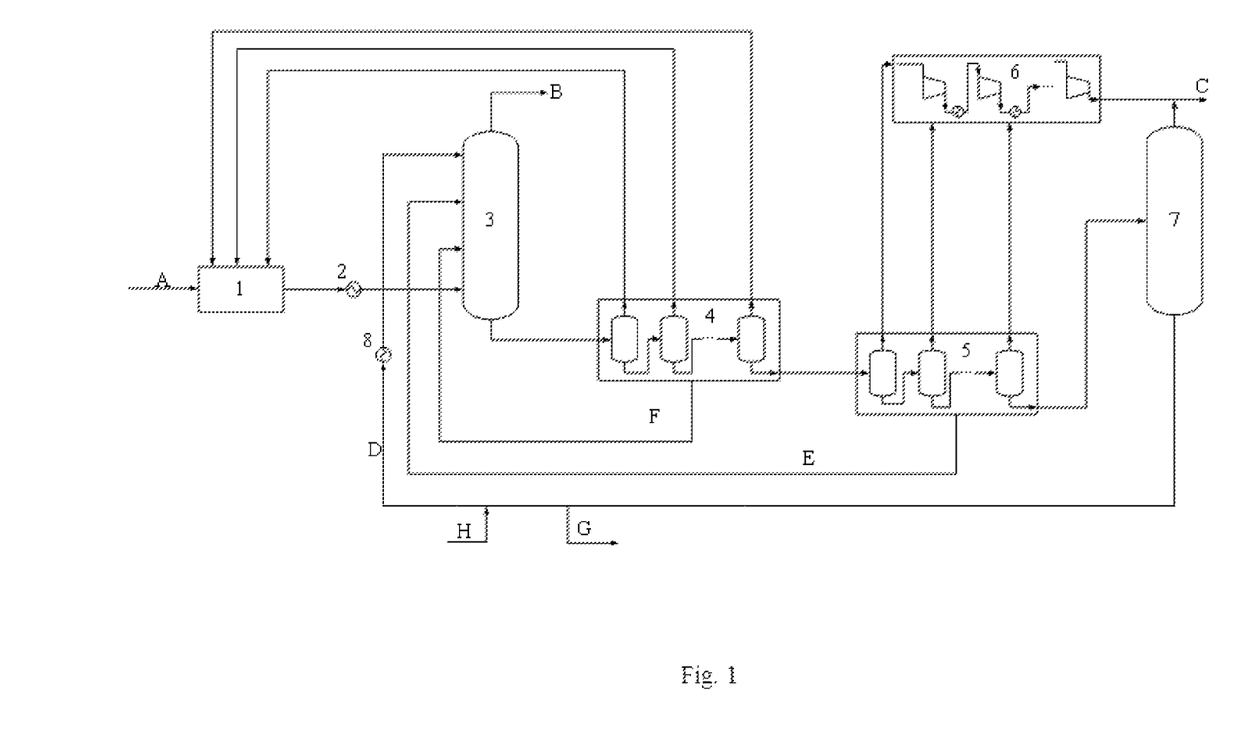
FIG. 1 is a structural schematic diagram of an energy-saving process and device for recovering C2 from refinery dry gas of the present invention.
Figure 2:
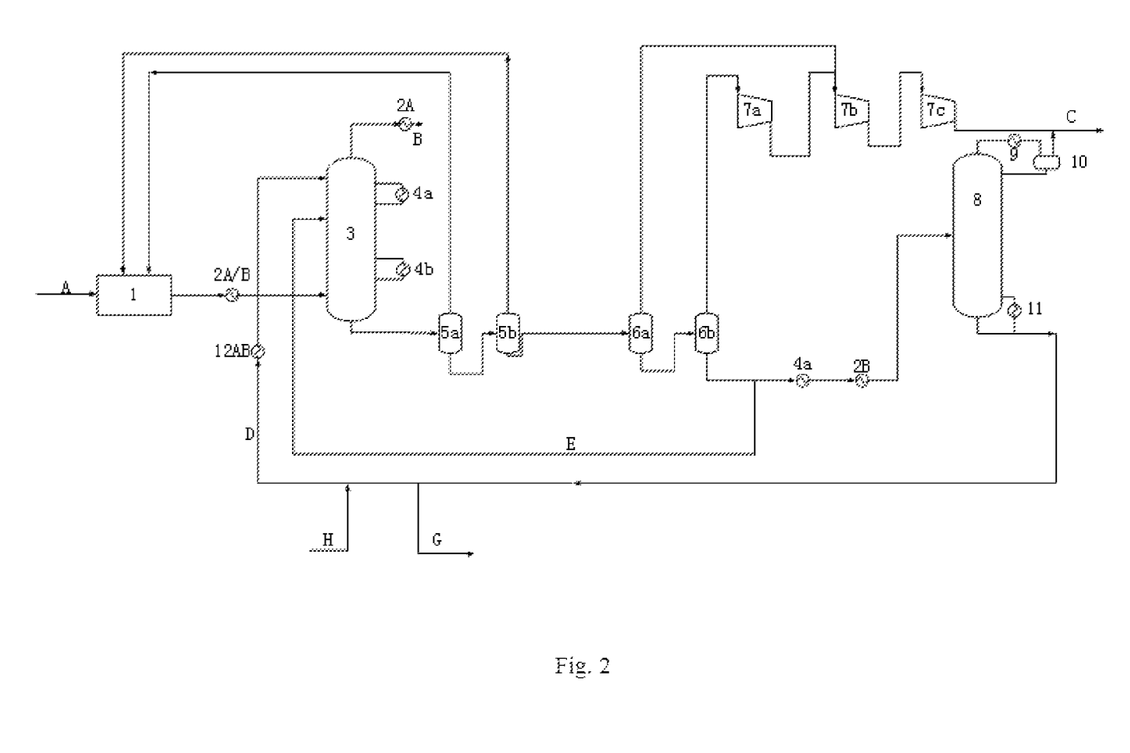
FIG. 2 is a schematic diagram of application of an energy-saving process and device for recovering C2 from refinery dry gas of the present invention.

FIG. 2 is taken as an example to describe an energy-saving process and device for recovering C2 from refinery dry gas provided by the present invention, wherein a plurality of dry gas precooling heat exchangers, multi-stage absorption tower intercoolers, C2 concentrated gas compressor stages, high-pressure zone flash tanks and low-pressure zone flash tanks can be arranged as required. In the embodiment, two dry gas precooling heat exchangers, two multi-stage absorption tower intercoolers, two high-pressure zone flash tanks and two low-pressure zone flash tanks are arranged, the C2 concentrated gas compression system is provided with three stages, only the circulation of the secondary lean solvent is set according to the optimization results, and no circulation of the semi-lean solvent is set.

The refinery dry gas obtained after treatment by the dry gas pretreatment, drying and compressor system 1 enters a separation unit provided by the present invention, and the specific flow is as follows: the refinery dry gas treated by raw material purification, dehydration and pressurization enters the 2A/B dry gas precooling heat exchanger for precooling and then enters the multi-stage absorption tower 3; the liquid phase at the bottom of the multi-stage absorption tower 3 enters the first-stage high-pressure zone flash tank 5a; the first-stage high-pressure zone flash tank 5a is connected with the second-stage high-pressure zone flash tank 5b in order; the top of the tank is rich in the gas phase of hydrogen and methane which are sent to different stages of the dry gas compression system 1 according to different pressures; the liquid phase at the bottom of the tank is sent to the first-stage low-pressure zone flash tank 6a; the first-stage low-pressure zone flash tank 6a is connected with the second-stage low-pressure zone flash tank 6b in order; the gas phase at the top of the tank is sent to different stages of the C2 concentrated gas compression system 7a-c according to different pressures; the liquid phase at the bottom of the tank is divided into two branches: one is recycled back to the multi-stage absorption tower 3 as the secondary lean solvent E for absorption, and the other is sent to the desorption tower 8 after cold energy recovery to recover C2 and C3; the gas phase at the top of the desorption tower 8, as C2 concentrated gas, is mixed with the C2 concentrated gas recovered under reduced pressure and then sent to the ethylene cracking unit as C2 concentrated gas; part of the liquid phase at the bottom of the desorption tower 8 is extracted as extracted C4; and fresh solvent liquid phase H is supplemented and mixed with the remaining liquid phase as the lean solvent D for circulation and absorption after cooling by the lean solvent cooling heat exchangers 12AB.

The recovery of dry gas after compression and drying in a refinery is taken as an example to explain the present invention. The composition of refinery dry gas is shown in Table 1:

TABLE 1

| Name | Refinery Dry Gas |
| --- | --- |
| Temperature, ° C. | 40 |
| Pressure, MpaG | 3.77 |
| Mass flow, kg/hr | 30542 |
| Molar flow, kmol/hr | 2010 |
| Composition, mol % | |
| Hydrogen | 41.73 |
| Carbon monoxide | 0.58 |

TABLE 1-continued

| Name | Refinery Dry Gas |
|---|---|
| Oxygen | 0.59 |
| Nitrogen | 7.18 |
| Methane | 28.29 |
| Ethane | 14.82 |
| Ethylene | 2.05 |
| Propane | 2.65 |
| Propylene | 0.30 |
| N-butane | 1.13 |
| Isobutane | 0.06 |
| 1-butylene | 0.02 |
| Isobutene | 0.01 |
| Cis-2-butene | 0.02 |
| N-pentane | 0.49 |
| Isopentane | 0.06 |
| N-hexane | 0.01 |
| Total | 100.00 |

The energy-saving process and device for recovering C2 from refinery dry gas of the present invention are used to separate the refinery dry gas to recover C2 and C3. The specific process flow is as follows:

The dry gas of each unit in the refinery enters the process of the present invention after pretreatment, compression, drying and mixing, and the pressure of the dry gas entering the process is 3.75 MpaG. The dry gas is cooled to −23° C. through the dry gas precooling heat exchanger 2A/B and sent to the bottom of the multi-stage absorption tower 3. In the multi-stage absorption tower 3, the absorbent is mixed C4 adsorbent, the total amount of the adsorbent is 58 t/h, comprising 23 t/h of lean solvent D and 35 t/h of secondary lean solvent E, the lean solvent D is injected from the top of the multi-stage absorption tower 3, and the secondary lean solvent E is injected from the middle part of the multi-stage absorption tower 3, which is absorbed by countercurrent contact with the dry gas. The number of theoretical plates of the multi-stage absorption tower 3 is 30, the operating pressure is 3.6 MpaG, the tower top temperature is −28.4° C., and the tower bottom temperature is −17.2° C. The liquid phase material from the bottom of the multi-stage absorption tower 3 is sent to the high-pressure zone flash tanks 5a-b for treatment, and the gas phase material from the top of the multi-stage absorption tower 3 is heat-exchanged with dry gas for cold energy recovery to 33° C. The gas phase material, mainly including unabsorbed methane and hydrogen, is sent to the fuel gas pipeline network or PSA unit for treatment. If sent to the fuel gas pipeline network, the gas phase material is preferably throttled and depressurized to 0.9 MpaG, and then heat-exchanged with dry gas for cold energy recovery to 33° C.

The liquid phase material from the bottom of the multi-stage absorption tower 3 is preferably depressurized to 1 MpaG and sent to the first-stage high-pressure zone flash tank 5a. The liquid phase at the bottom of the first-stage high-pressure zone flash tank 5a is preferably depressurized to 0.3 MpaG and sent to the second-stage high-pressure zone flash tank 5b. The gas phase at the top of the high-pressure zone flash tanks 5a-b (rich in hydrogen and methane) is sent to different stages of the dry gas compression system according to different pressures, and the liquid phase at the bottom of the second-stage high-pressure zone flash tank 5b is sent to the first-stage low-pressure zone flash tank 6a.

The liquid phase from the second-stage high-pressure zone flash tank 5b is preferably depressurized to 0.13 MpaG and sent to the first-stage high-pressure zone flash tank 6a. The liquid phase returned to the bottom of the first-stage low-pressure zone flash tank 6a is preferably depressurized to 0 MpaG and sent to the second-stage low-pressure zone flash tank 6b. The gas phase at the top of the first-stage low-pressure zone flash tank 6a is sent to the first-stage C2 concentrated gas compressor 7a, the gas phase at the top of the second-stage low-pressure zone flash tank 6b is sent to the second-stage C2 concentrated gas compressor 7b, and the C2 concentrated gas (1 MpaG) pressurized by the C2 concentrated product compression system 7a-c is sent to the ethylene cracking furnace. The liquid phase at the bottom of the second-stage low-pressure zone flash tank 6b is divided into two branches: one is recycled and absorbed as the secondary lean solvent E (35 t/h, −59° C.), and the other passes through the multi-stage absorption tower intercooler 4a and the dry gas precooling heat exchanger 2B in order for cold energy recovery to 33° C. and enters the C2 desorption tower 8.

The liquid phase from the bottom of the second-stage low-pressure zone flash tank 6b is sent to the middle part of the desorption tower 8 after cold energy recovery and pressurization. The number of theoretical plates of the desorption tower is 30, the operating pressure is preferably 3.5 MpaG, the tower top temperature is 40.8° C., and the tower bottom temperature is 152° C. The condenser 9 at the top of the desorption tower 8 is condensed to 40.8° C. by wet air cooling or circulating cooling water, and the reboiler 11 at the bottom of the tower is heated with low-pressure steam or hot oil. The gas phase (rich in C2 and C3) at the top of the desorption tower 8 is mixed with the C2 concentrated gas recovered by vacuum flashing and sent to the ethylene cracking furnace. Most of the liquid phase at the bottom of the desorption tower 8 is recycled and absorbed as the lean solvent D (23 t/h) after fresh solvent is supplemented. The lean solvent D is cooled to 0° C. with −6° C. propylene refrigerant through the lean solvent cooling heat exchanger 12A, then cooled to −35° C. with −40° C. propylene refrigerant through the lean solvent cooling heat exchanger 12B and sent to the top of the multi-stage absorption tower 3.

In the implementation method, the composition of the C2 concentrated gas is shown in Table 2, and the composition of the lean solvent and the secondary lean solvent is shown in Table 3.

TABLE 2

| Name | C2 Concentrated Gas |
|---|---|
| Temperature, ° C. | 40 |
| Pressure, MpaG | 1.06 |
| Mass flow, t/hr | 12456 |
| Molar flow, kmol/hr | 389 |
| Composition, mol % | |
| Hydrogen | 0.01 |
| Oxygen | 0.02 |
| Nitrogen | 0.02 |
| Methane | 4.01 |
| Ethane | 73.22 |
| Ethylene | 6.80 |
| Propane | 12.13 |
| Propylene | 1.43 |
| N-butane | 1.18 |
| Isobutane | 1.05 |
| 1-butylene | 0.02 |
| Isobutene | 0.01 |
| Cis-2-butene | 0.01 |
| N-pentane | 0.08 |
| Isopentane | 0.01 |

In the embodiment, the recovery rate of C2 is 91.4%, and the recovery rate of ethane is 94.9%.

TABLE 3

| Name | Lean Solvent | Secondary Lean Solvent |
|---|---|---|
| Mass flow, t/hr | 23 | 35 |
| Molar flow, kmol/hr | 382.2 | 665.5 |
| Composition, mol % | | |
| Methane | 0.00 | 0.04 |
| Ethane | 0.66 | 21.06 |
| Ethylene | 0.01 | 0.93 |
| Propane | 4.22 | 9.99 |
| Propylene | 0.32 | 1.03 |
| N-butane | 45.96 | 33.25 |
| Isobutane | 27.02 | 16.70 |
| 1-butylene | 0.52 | 0.40 |
| Isobutene | 0.31 | 0.25 |
| Trans-2-butene | 0.05 | 0.04 |
| Cis-2-butene | 0.49 | 0.38 |
| N-pentane | 18.19 | 14.16 |
| Isopentane | 1.98 | 1.54 |

In the embodiment, the energy-saving process and device for recovering C2 from refinery dry gas of the present invention, the traditional middle cold oil absorption process (patent CN 101063048A) and the shallow cold oil absorption process (CN 109553504A) all adopt the dry gas feed provided by the present invention. The comparison of energy consumption is shown in Table 4, wherein the electric power includes the electric power consumed by refrigeration.

TABLE 4

| | Shallow Cold Oil Absorption Process | Traditional Middle Cold Oil Absorption Process | The present invention |
|---|---|---|---|
| Electricity/kW | 6897 | 10600 | 6592 |
| Low low-pressure steam/kW | 10187 | 5000 | 0 |
| Low-pressure steam/kW | 1665 | 0 | 3030 |
| Hot water/kW | 0 | 2532 | 0 |
| Circulating water/kW | 19871 | 4606 | 10828 |
| Comprehensive energy consumption/ (standard oil kg/h) | 3290.28 | 3453.77 | 2187.95 |

The embodiment of the present invention is described above. In the embodiment, the circulation amount of the lean solvent is only ¼ of the total solvent amount, and half of the C2 concentrated gas is recovered by means of flash desorption, resulting in a significant reduction in the treatment capacity of the C2 desorption tower at the main energy consumption location, which greatly reduces the total energy consumption. Through the optimization of the process flow, the goals of saving energy and reducing investment are achieved. It can be seen from Table 4 that compared with the flow of the traditional middle cold oil absorption technology and the existing shallow cold oil absorption technology, the process of the present invention can reduce the total comprehensive energy consumption by 33.5% and 36.65% respectively. In addition, only two main equipment towers are arranged in the present invention, and the equipment size is small, which reduces the total investment cost.

The embodiment is illustrative only, not all of the embodiments. All other embodiments improved or adjusted by those ordinary skilled in the art will belong to the protection scope of the present invention.

The invention claimed is:

1. An energy-saving process for recovering C2 from refinery dry gas, wherein the process flow is as follows:
   (1) sending refinery dry gas treated through deacidification, drying, compression and cooling by a dry gas pretreatment system to a multi-stage absorption tower, sending the gas phase at the top of the tower obtained from the multi-stage absorption tower to a fuel gas pipeline network or PSA unit, and sending the liquid phase at the bottom of the tower obtained from the multi-stage absorption tower to a high-pressure flash zone;
   (2) arranging multiple stages of high-pressure zone flash tanks in the high-pressure flash zone, and returning the gas phase obtained by flash to the compression section of the dry gas pretreatment system; and recycling one part of the obtained liquid phase back to the multi-stage absorption tower as a semi-lean solvent, and sending the other part to a low-pressure flash zone for treatment; and the multiple stages of high-pressure zone flash tanks are successively depressurized and connected in series, and the pressure of the last flash tank is 0.1~0.3 MpaG;
   (3) arranging multiple stages of low-pressure zone flash tanks in the low-pressure flash zone, sending the gas phase, C2 concentrated gas to a C2 concentrated gas compressor system, recycling one part of the obtained liquid phase back to the multi-stage absorption tower as a secondary lean solvent, and sending the other part to a desorption tower; and the multiple stages of low-pressure zone flash tanks are successively depressurized and connected in series, and the pressure of the last flash tank is 0~0.1 MpaG;
   (4) mixing the gas phase obtained from the desorption tower with the gas phase from the low-pressure flash zone and sending to an ethylene cracking furnace as C2 concentrated gas, returning part of the liquid phase obtained from the desorption tower to the multi-stage absorption tower as a lean solvent, sending the other part out of the battery limit as C4, and supplementing the C4 from the battery limit as fresh adsorbent.

2. The energy-saving process for recovering C2 from refinery dry gas according to claim 1, wherein the treatment method of the multi-stage absorption tower is as follows: the cooled refinery dry gas is supplied to the multi-stage absorption tower to be in contact with the mixed C4 adsorbent, the number of theoretical plates of the multi-stage absorption tower is 30~60, the operating pressure is 3~5 MpaG, the tower top temperature is −15° C. ~−35° C., and the tower bottom temperature is −10° C. ~−30° C.

3. The energy-saving process for recovering $C_2$ from refinery dry gas according to claim 1, wherein in the liquid phase obtained from the high-pressure flashzone: the liquid phase entering the low-pressure flash zone is the liquid phase of the last flash tank, the semi-lean solvent is the liquid phase of each flash tank, the feed plate of the semi-lean solvent is 20~45, and the temperature of the semi-lean solvent is −10° C. ~−40° C.

4. The energy-saving process for recovering C2 from refinery dry gas according to claim 1, wherein in the liquid phase obtained from the low-pressure flash zone: the liquid phase sent to the desorption tower is the liquid phase of the last flash tank, the secondary lean solvent is the liquid phase of each flash tank, the feed plate of the secondary lean solvent is 5~25, and the temperature of the secondary lean solvent is −30° C. ~−70° C.

5. The energy-saving process for recovering C2 from refinery dry gas according to claim 1, wherein the treatment method of C2 concentrated gas compression is as follows: the pressure of the gas phase obtained from the low-pressure flash zone is increased to 0.5~2 MPaG.

6. The energy-saving process for recovering C2 from refinery dry gas according to claim 5, wherein the C2 concentrated gas compression is multi-stage compression.

7. The energy-saving process for recovering C2 from refinery dry gas according to claim 1, wherein the cooling treatment method is as follows: the treated refinery dry gas is cooled to −15° C. ~−40° C., and propylene refrigeration is used for cooling; and in combination with the operating temperature of other equipment in the process, the propylene refrigeration adopts primary to tertiary refrigeration.

8. The energy-saving process for recovering C2 from refinery dry gas according to claim 7, wherein the C4 adsorbent is C4 fraction containing n-butane and isobutane, saturated liquefied gas containing saturated C3 fraction and C4 fraction, or C5 fraction containing n-pentane and isopentane.

9. The energy-saving process for recovering C2 from refinery dry gas according to claim 8, wherein in the C4 adsorbent: the recycled lean solvent is composed of 80~95 mol % of C4 and the balance of C3 and C5; and the recycled secondary lean solvent is composed of 50~80 mol % of C4, and the recycled semi-lean solvent is composed of 30~70 mol % of C4.

10. The energy-saving process for recovering C2 from refinery dry gas according to claim 1, wherein the treatment method of the desorption tower is as follows: the liquid phase material obtained from the low-pressure flash zone is supplied to the C2 desorption tower for separation, the number of theoretical plates of the absorption tower is 20~60, the operating pressure is 0.5~4 MpaG, the tower top temperature is −35° C.~40° C., and the tower bottom temperature is 60° C.~130° C.

11. The energy-saving process for recovering C2 from refinery dry gas according to claim 10, wherein the lean solvent returned to the multi-stage absorption tower for recycling is cooled to −15° C. ~−40° C., and returned to the top of the multi-stage absorption tower as lean adsorbent for recycling.

12. An energy-saving device used in the energy-saving process for recovering C2 from refinery dry gas according to claim 1, wherein the energy-saving device comprises a dry gas pretreatment system, a multi-stage absorption tower, high-pressure zone flash tanks, low-pressure zone flash tanks, a desorption tower, a C2 concentrated gas compressor system and a lean solvent cooling heat exchanger;

the outlet of the dry gas pretreatment system is communicated with a dry gas precooler;
the outlet of the dry gas precooler is communicated with the bottom of the multi-stage absorption tower;
the bottom of the multi-stage absorption tower is communicated with the first-stage high-pressure zone flash tank;
the top of the high-pressure zone flash tank is communicated with the dry gas pretreatment system, and the bottom of each stage of high-pressure zone flash tank is connected with the inlet of the next stage of flash tank, wherein a pipeline at the bottom of one or multiple stages of flash tanks is connected with the lower part of the multi-stage absorption tower, and the bottom of the last stage of flash tank is connected with the inlet of the first-stage low-pressure zone flash tank;
the top of the low-pressure zone flash tank is communicated with the C2 concentrated gas compressor system, and the bottom of each stage of low-pressure zone flash tank is connected with the inlet of the next stage of flash tank, wherein a pipeline at the bottom of one or multiple stages of flash tanks is connected with the middle part of the multi-stage absorption tower, and the bottom of the last stage of flash tank is connected with the inlet of the desorption tower;
the top of the desorption tower is connected with a production pipeline of C2 concentrated gas products, and a pipeline at the bottom of the tower is divided into two branches:
one is communicated with the lean solvent cooling heat exchanger, and the other is an extracted C4 pipeline; and a pipeline for supplementing fresh C4 is connected with a lean solvent pipeline;
the outlet of the lean solvent cooling heat exchanger is connected with the top of the multi-stage absorption tower.

* * * * *